US00PP25301P2

(12) United States Plant Patent
Warren

(10) Patent No.: US PP25,301 P2
(45) Date of Patent: Feb. 24, 2015

(54) RED MAPLE TREE NAMED 'JFS-KW78'

(50) Latin Name: *Acer rubrum*
Varietal Denomination: JFS-KW78

(71) Applicant: J. Frank Schmidt & Son Co., Boring, OR (US)

(72) Inventor: Keith S. Warren, Gresham, OR (US)

(73) Assignee: J. Frank Schmidt & Son Co., Boring, OR (US)

( * ) Notice: Subject to any disclaimer, the term of this patent is extended or adjusted under 35 U.S.C. 154(b) by 184 days.

(21) Appl. No.: 13/815,463

(22) Filed: Mar. 5, 2013

(51) Int. Cl.
*A01H 5/00* (2006.01)

(52) U.S. Cl.
USPC ..... Plt./224

(58) Field of Classification Search
USPC ..... Plt./224
See application file for complete search history.

*Primary Examiner* — Anne Grunberg
(74) *Attorney, Agent, or Firm* — Klarquist Sparkman, LLP

(57) ABSTRACT

A new variety of red maple with a unique combination of characteristics, combining a tightly fastigiate branching habit, an extremely narrow to columnar form, small leaves with long acuminate tips that produce a delicate appearance, and bright fall color.

10 Drawing Sheets

Latin name of the genus and species of the plant claimed: *Acer rubrum.*

Variety denomination: 'JFS-KW78'.

BACKGROUND OF THE INVENTION

In May of 1995, I collected open pollinated seed from a single specimen of *Acer rubrum* 'Armstrong' (unpatented) growing in Boring, Oreg. My goal was to eventually select an improved columnar form of *Acer rubrum*. I immediately sowed this seed in seedbeds in a nursery in Boring, Oreg. The seed germinated quickly and grew well. I allowed these seedling trees to grow for two seasons and then dug them in January of 1997. I was able to harvest approximately 250 small seedling trees. From these, I saved the largest 162 seedlings and planted them out into a row in the same nursery in May of 1997. The other seedlings were destroyed. I then allowed these seedling trees to grow for three growing seasons and regularly evaluated them, looking for unusual forms for selection. From these 162 trees, I selected the three narrowest growing trees in the fall of 1999 and destroyed the others. One of these three trees was 'JFS-KW78'. I selected it because it was the narrowest growing and most compact of the trees in the row. I planted 'JFS-KW78' and the two sibling trees in a long term evaluation block in the spring of 2000 along with other selected forms of *Acer rubrum*. Over the next eight years, I evaluated these trees and determined that 'JFS-KW78' was the narrowest and most compact of the trees I had selected. I destroyed the two sibling trees as inferior in form.

In August of 2005, August of 2007, and August of 2009, I propagated small test plots by chip budding on *Acer rubrum* rootstock in a nursery in Canby, Oreg., and a nursery in Boring, Oreg. Each one of these test plots consisted of approximately 20 trees which were grown for evaluation purposes for two years, then destroyed. In 2007 I rooted 38 trees from softwood cuttings in a nursery in Boring, Oreg. These were also planted in a nursery row test plot in Boring, Oreg. in 2009 and evaluated over the next two growing seasons. These trees were dug in January 2012 and transplanted into a stock block in the same nursery for future propagation.

In the summer of 2009, I sent shoot tips of my new maple to a micropropagation lab in Gervais, Oreg. All micropropagated plants were sent to the same Boring, Oreg. and Canby nurseries where they have been planted and all still remain in the field.

All of this asexual propagation in Canby and Boring, Oreg. by budding on *Acer rubrum* rootstock, by softwood cuttings, and by micropropagation has shown that the characteristics of my new tree are firmly fixed in successive generations. Testing, evaluation, and comparison of 'JFS-KW78' with seedlings of the species and existing commercial cultivars of *Acer rubrum* has convinced me that my new tree has superior form and appearance for landscape use.

Classification: In recent years, some authors have reclassified some cultivars of *Acer rubrum* as the hybrid species *Acer×freemanii*. I have followed the classification published by Santamour and McArdle of the U.S. National Arboretum which classified the seed parent of my tree, 'Armstrong', as *Acer rubrum* (Santamour and McArdle, Checklist of Cultivated Maples 1. *Acer rubrum* L., Journal of Arboriculture 8(4), April 1982). As all of the trees I have raised from seed of 'Armstrong', including my new tree, most closely resemble true *Acer rubrum*, I believe this is correct.

SUMMARY

This new cultivar possesses a unique combination of characteristics in that it combines tightly upright fastigiate branching, an extremely narrow to columnar form, small leaves with long acuminate tips that give it a delicate appearance, and bright fall color.

BRIEF DESCRIPTION OF THE DRAWINGS

The colors of an illustration of this type may vary with lighting conditions and, therefore, color characteristics of this new variety should be determined with reference to the observations described herein, rather than from these illustrations alone.

DETAILED BOTANICAL DESCRIPTION

Figure 1:
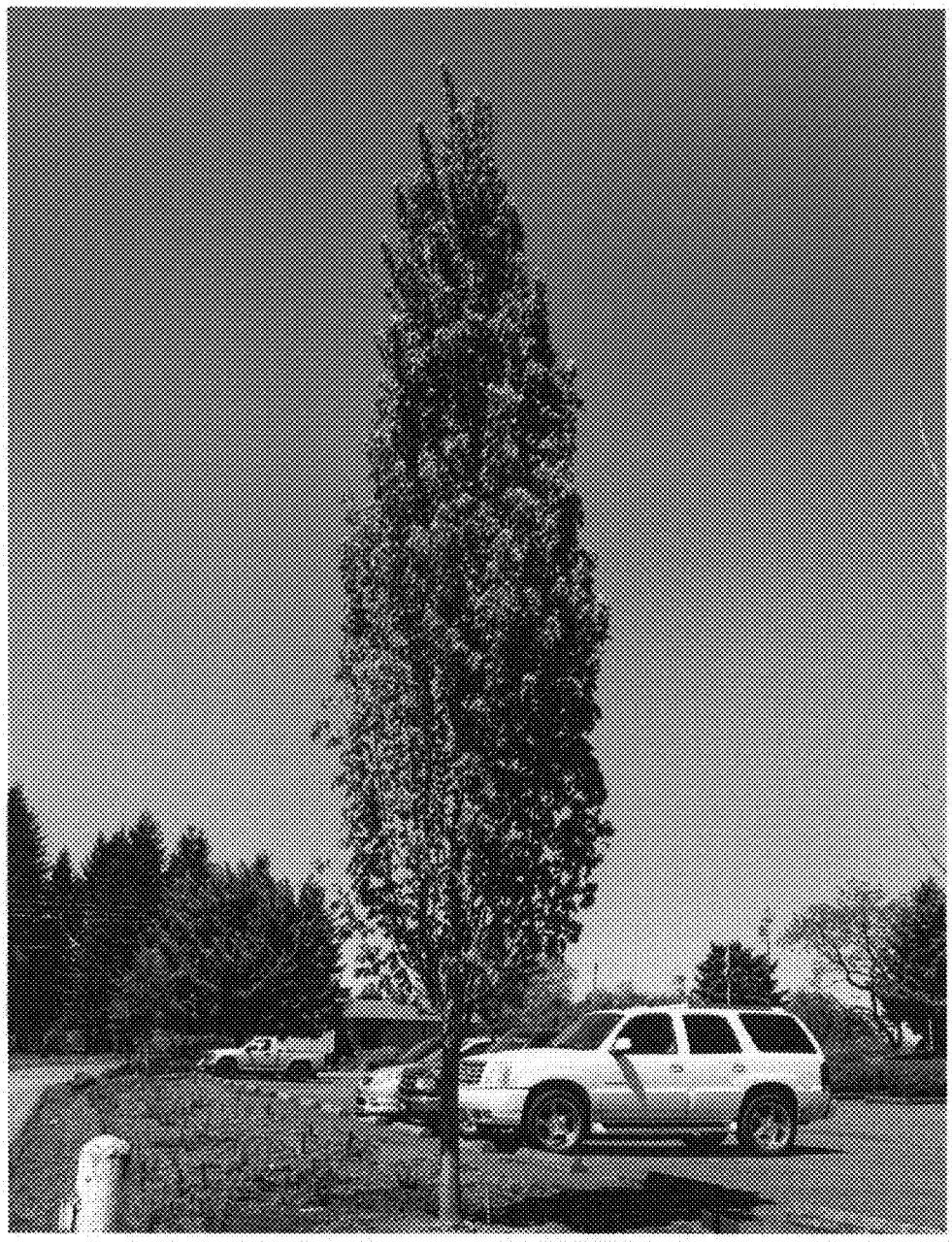
FIG. 1: illustrates the original tree at 16 years of age in summer foliage, showing its columnar to extremely narrow shape.
Figure 2:
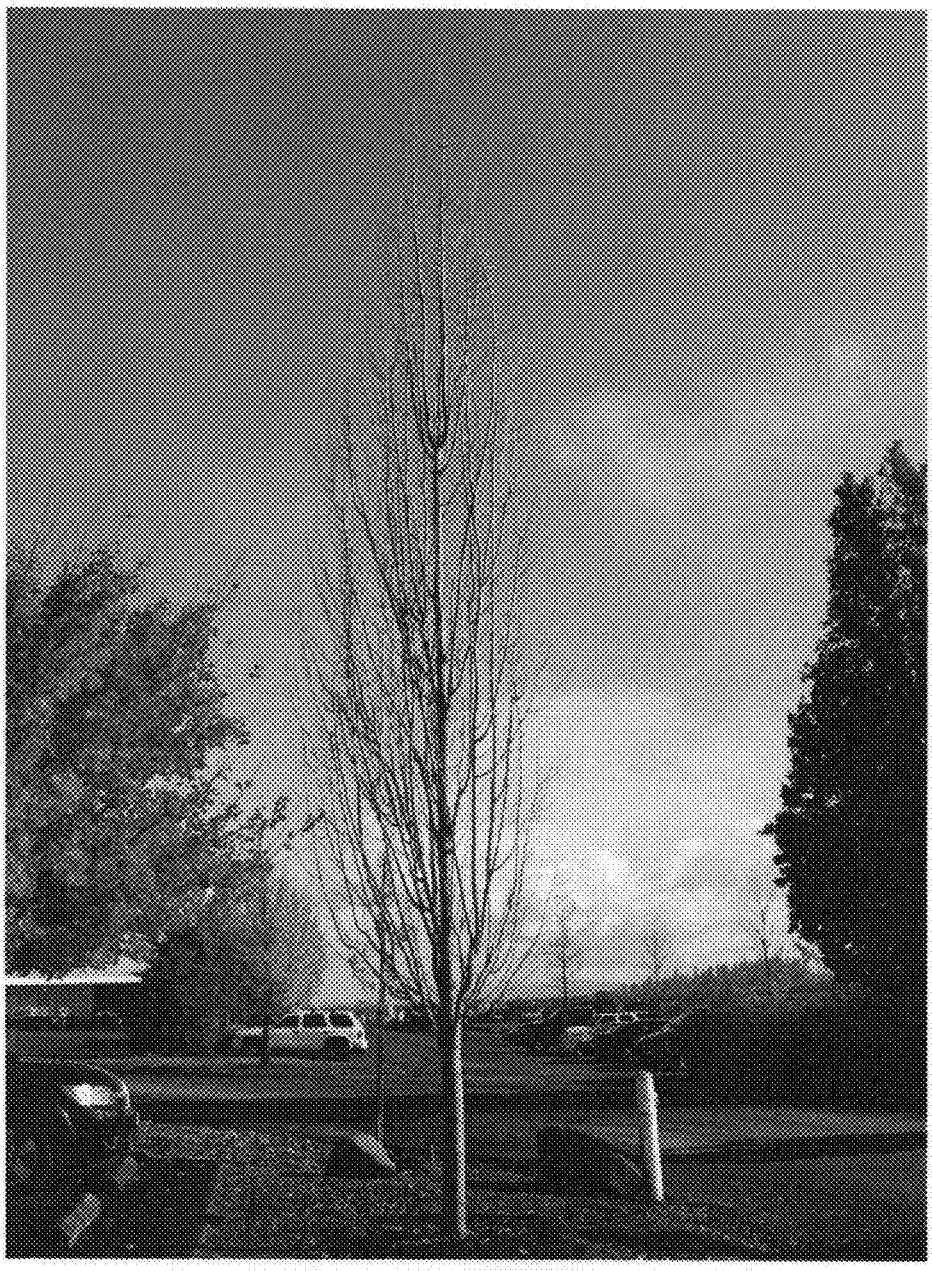
FIG. 2: illustrates the original tree at 16 years of age after defoliation in the fall, showing its tightly upright, fastigiate branching habit.
Figure 3:
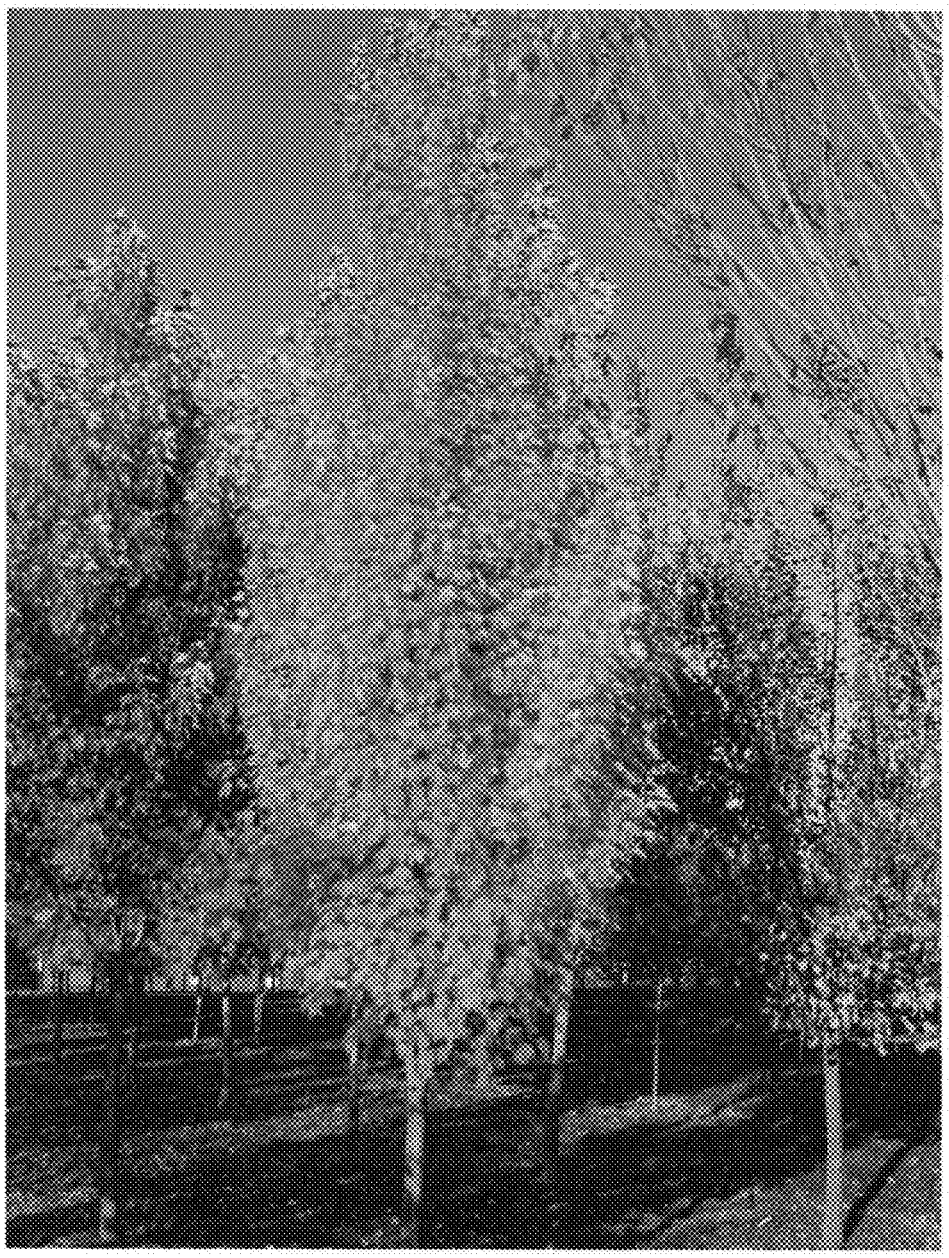
FIG. 3: illustrates the original tree (center of the photo) in fall color in the evaluation block at 11 years of age, illustrating the brightness of the fall color, the tightly upright shape, and densely held small leaves which give it a delicate appearance.
Figure 4:
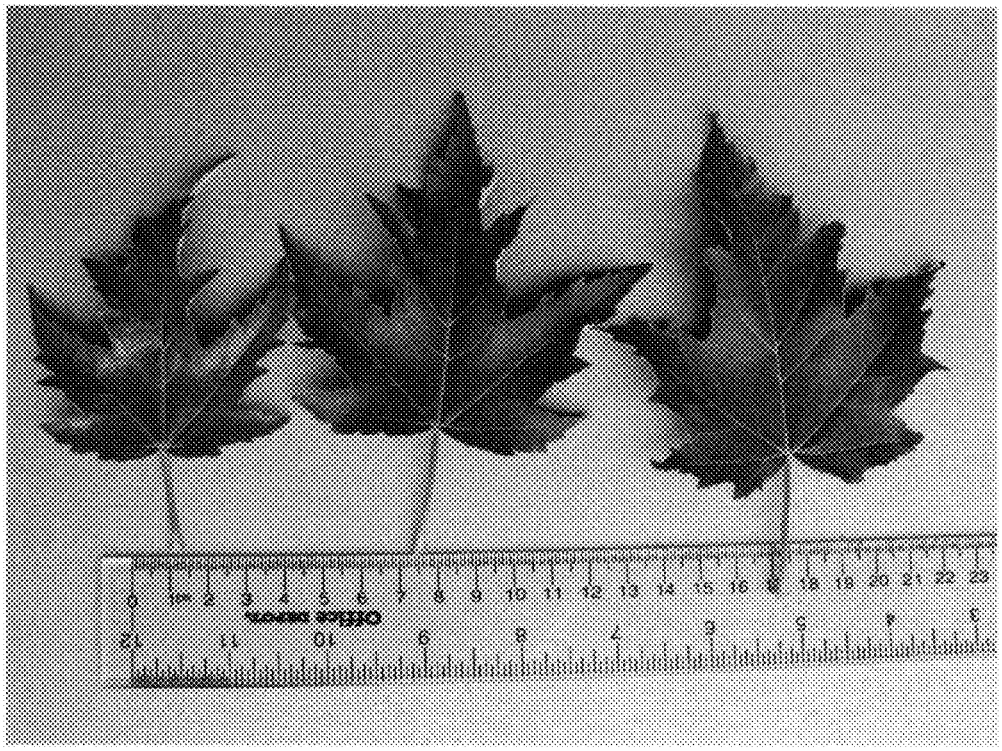
FIG. 4: is a close up of the top surface of summer foliage of my new variety, showing typical leaf shape and color, and the unusually long, slender center lobe with a long acuminate tip.
Figure 5:
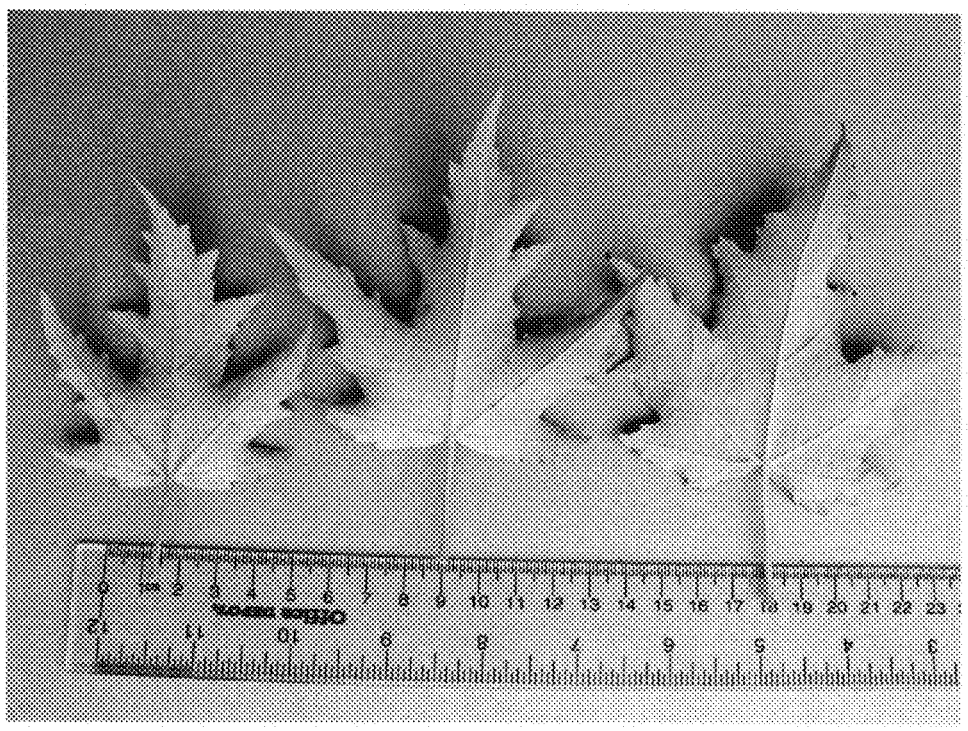
FIG. 5: is a close up of the lower surface of summer foliage of my new variety, showing typical leaf shape and color.
Figure 6:
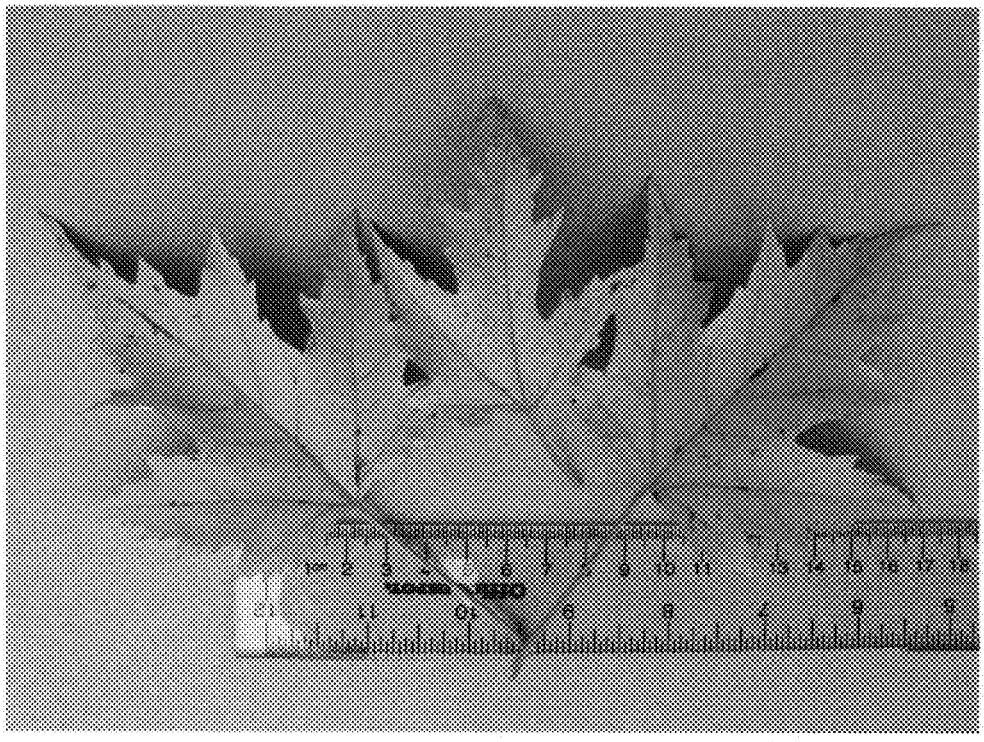
FIG. 6: is a close up of the top surface of fall foliage of my new variety, showing peak fall color.
Figure 7:
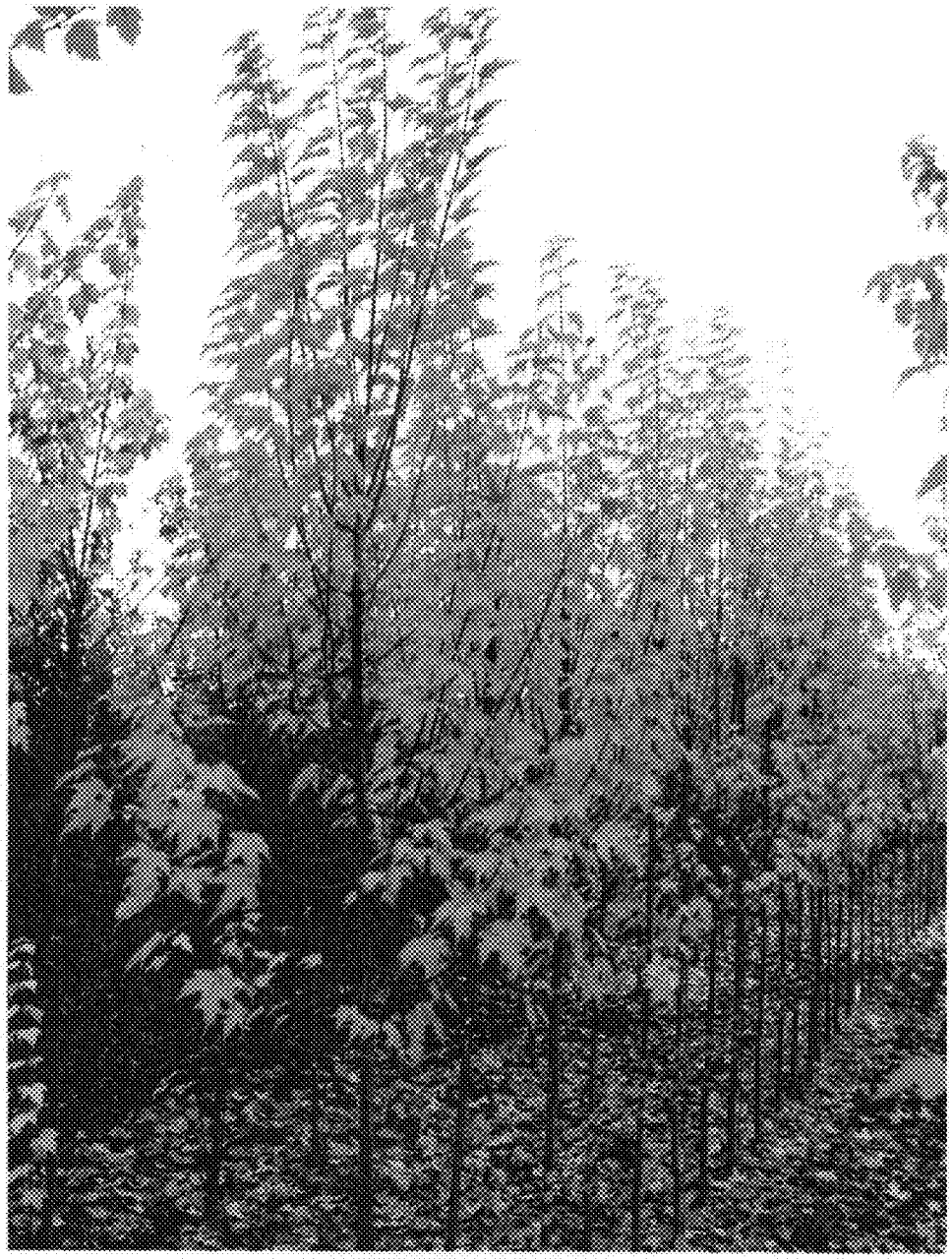
FIG. 7: illustrates two year old trees of my new variety in a nursery row, showing the upright form and branches that sweep upward in branch angle from wide crotch angles in the lower portion of the canopy and branches that ascend strongly upward from narrower angles near the top of the tree.
Figure 8:
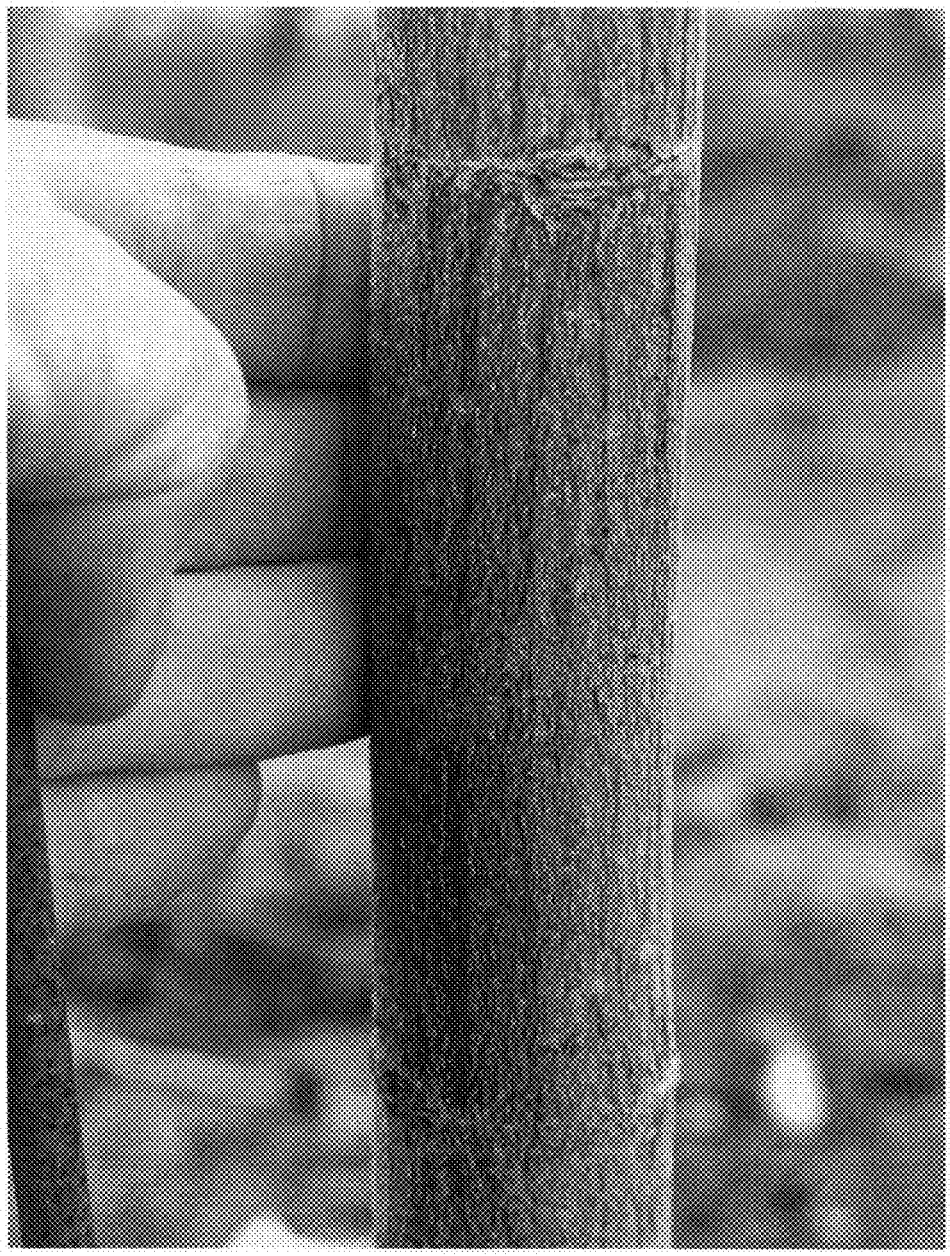
FIG. 8: is a close up of the immature trunk bark of a two year old tree of my new variety, showing the thin, faint vertical color striations.
Figure 9:
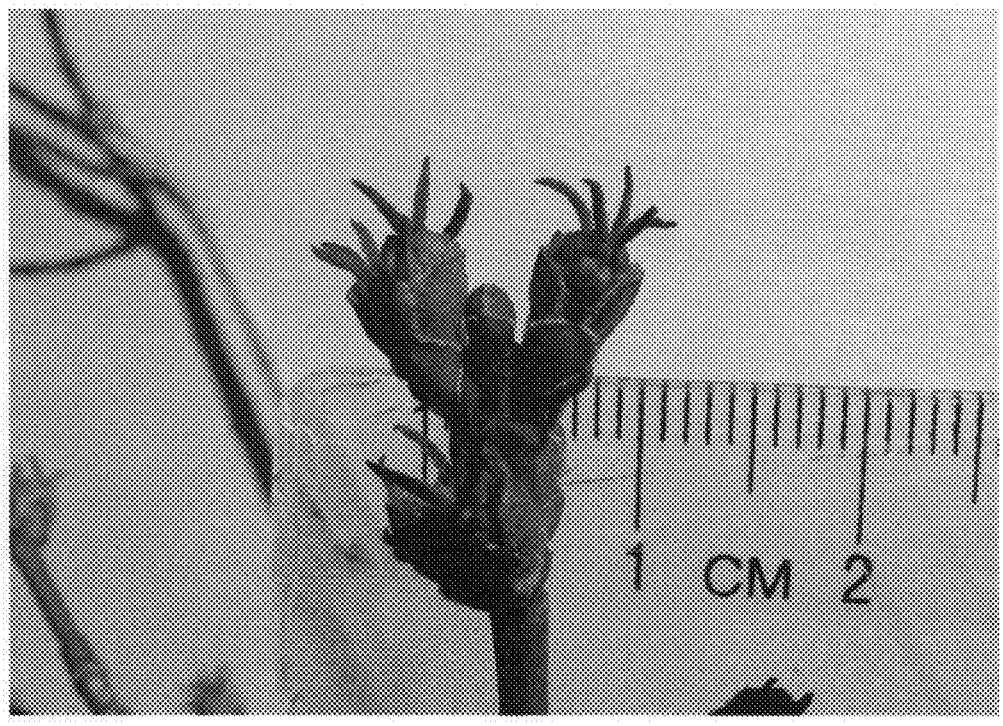
FIG. 9: is a close up of the flowers of my new variety.
Figure 10:
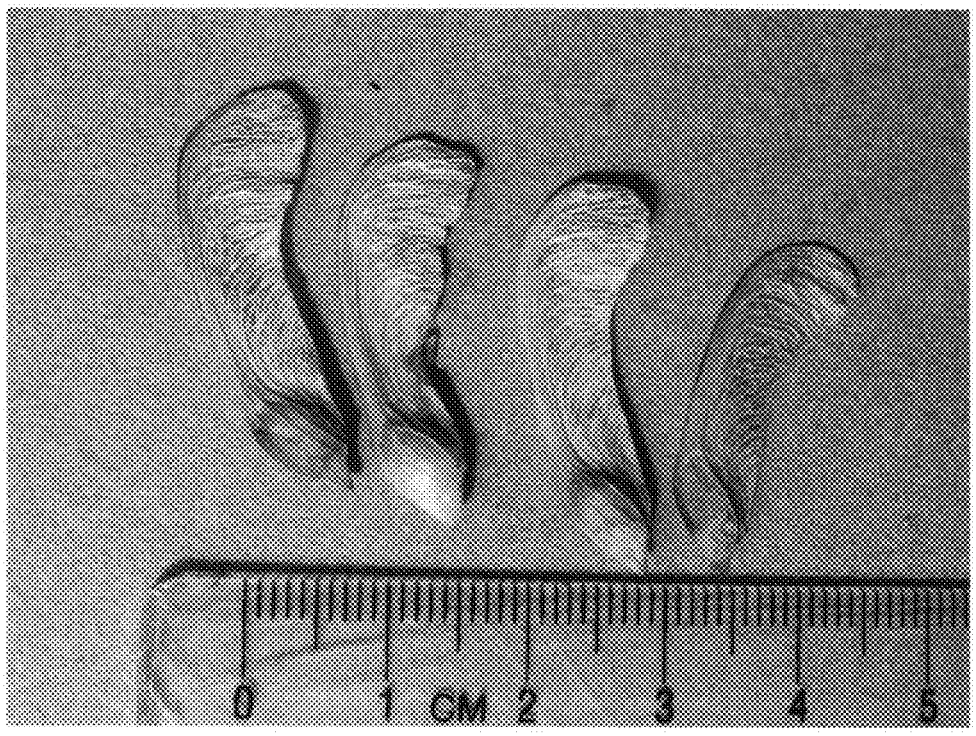
FIG. 10: is a close up of the seeds of my new variety.

The following detailed description of the 'JFS-KW78' variety is based on observations of the original tree and one, two, and three year old progeny. The observed progeny were trees which were growing in Boring, Oreg. and Canby, Oreg. The following is a detailed description of my new red maple tree is made with color descriptions using terminology in accordance with The Royal Horticultural Society (London) Colour Chart©, 1986.

Scientific name: *Acer rubrum* 'JFS-KW78'.

Parentage:

*Seed parent.*—*Acer rubrum* 'Armstrong'.

*Pollen parent.*—Unknown tree of the species *Acer rubrum.*

Tree:

*Overall shape.*—A tightly fastigiate branching habit causes the tree to develop a dense, upright, columnar to extremely narrow oval shape.

*Height.*—10.5 meters at 17 years of age.

*Width.*—2.3 meters at 17 years of age.

*Growth rate.*—Moderate. Similar to the growth rate of *Acer rubrum*, slower than the seed parent 'Armstrong'.

*Diameter.*—14.9 cm at 10 cm height, 12.9 cm at 1 meter, at 17 years of age.

*Trunk.*—Straight, strongly upright, single stem with a very gradual taper.

*Trunk bark texture.*—Smooth on 1 and 2 year old trees. Smooth on original tree at 17 years of age.

*Trunk bark color.*—Immature bark color on 1 year old trees: Greyed-Orange 163A to Greyed-Orange 164A measured at 1 meter height in early October. Immature bark color on 2 year old trees: Greyed-Orange 164A to Greyed-Orange 165A measured at 1 meter height in early October. Thin, faint vertical color striations are seen on the two year old trunk, with color varying in the range stated. Mature bark color: Grey-Green 197B to Grey-Green 198C without striations.

*Trunk lenticels.*—Not visible on trunk of original tree at 17 years of age.

*Primary branches.*—On the original tree at 17 years of age: strongly fastigiate and ascending, curving upward to nearly vertical orientation from crotch angles that are generally 30° to 60°. Longest primary branches on the original tree at 17 years of age are 4 to 5 meters long. On two year old trees in a nursery in Boring, Oreg., branches are tightly upsweeping to produce a very narrow form.

*Branch color.*—Young branches, during their first season of growth, are smooth barked, Greyed-Orange 174B to Grey-Brown 199A as they mature in the fall. They become Greyed-Orange 172C to Greyed-Orange 165C in the winter. During their second season, branches are Greyed-Orange 165A to Greyed Orange-165B as they mature in the fall then become Greyed-Orange 177B to Grey-Brown 199B in the winter.

*Branch lenticels.*—On branches of trees of 2 years of age: broadly oval to oblong, typically 1 to 2 mm long by 0.5 mm to 1.0 mm wide, with a density averaging 2 per square centimeter. Color is Orange-White 159B.

*Dormant buds.*—Ovoid with acute to obtuse tip, with imbricate scales, very slightly appressed against the twig, 2 mm to 5 mm long by 1 mm to 2.5 mm in diameter, Greyed-Orange 177B to Greyed-Purple 183A.

*Bud break.*—Bud break averages April 8 under Boring, Oreg. conditions. Bud break is about 5 days later than the average for the species.

*Internodes.*—Average length is 6.7cm when measured 30 cm proximal from the tip of mature branches on 2 yr nursery trees.

*Hardiness.*—Has tolerated field temperatures to 10 degrees F. without damage in Boring, Oreg. and Canby, Oreg. It is believed to have Zone 4 cold hardiness similar to other plants of this species.

*Disease and insect resistance.*—Appears similar to the species with no differences noted.

Leaves: Except as otherwise noted, observations are from twenty vigorous growth leaves on trees grown in a nursery in Boring, Oreg.

*Arrangement.*—Opposite.

*Type.*—Simple.

*Texture.*—Smooth on upper surface. Slightly wrinkled by veins on lower surface.

*Sheen.*—Dull to slightly satiny on upper surface. Dull on lower surface.

*Length.*—7 to 15 cm. on 1 and 2 year old trees (leaf blade, excluding petiole).

*Width.*—7 to 13 cm. on 1 and 2 year old trees (leaf blade, excluding petiole).

*Petioles.*—4 cm to 7 cm long×1 mm to 2 mm in diameter when measured on one and two year old trees. Color on the upper surface where exposed to sunlight is Red 46A. Where petiole is in shade, color of upper surface will vary to Yellow-Green 145C. Lower surface of petiole is Yellow-Green 145C.

*Overall shape.*—Palmate with three main lobes, and six to eight minor lobes. Lobe tips are acuminate. The longest lobe is central and is typically 55% to 65% of the length of the leaf blade. The longest two side lobes are typically 30% to 45% of the length of the leaf blade.

*Margin*.—Irregularly coarsely serrate. Slightly undulate.

*Tip*.—Long acuminate.

*Base*.—Cordate to truncate or very broadly acute. Leaves on young trees generally have cordate to truncate bases, while leaves on trees older than three years have leaves that may vary to broadly acute.

*Stipules*.—None.

*Spring leaf color*.—First emerging leaves are Greyed-Orange 176A to Greyed-Purple 183A on top surface. Lower surface of first emerging leaves is Greyed-Orange 174B with a tint of Yellow-Green 145A.

*Summer leaf color*.—Upper leaf surface: Green 137A to Yellow-Green 147A. Lower leaf surface: Green 138C. Vein: Yellow-Green 145C.

*Fall leaf color*.—Individual leaves vary from Yellow-Orange 23B to Red 42B on top surface, and lower surface is Yellow-Orange 23D to Orange 24B. From a distance, the overall color of the tree with foliage in mass appears similar to Orange-Red 30B.

*Timing of fall leaf color*.—Average dates for original tree in Boring, Oreg. Onset: October 8. Peak: October 20. Latest extent of fall color: November 2.

*Defoliation*.—After peak fall color, the tree gradually loses the brightness of its fall color and defoliation begins. In Boring, Oreg., the original tree is typically 50% defoliated by October 28, and completely defoliated by November 3.

*Pubescence*.—New unfolding leaves in spring are very sparsely pubescent on veins on the underside and glabrous on top. Summer leaves are sparsely to moderately pubescent on the underside and generally glabrous on the upper surface except for a few hairs along the veins.

*Persistence*.—The tree is deciduous.

Flowers:

*Overall*.—A small nearly sessile to short stalked umbel of generally three to five flowers. Flowers are held tightly at first opening and are surrounded by four bud scales. The pedicels gradually elongate as flower mature. The tree only produces pistillate (female) flowers. Although the flowers are female, they do produce small, vestigial, non-functional anthers.

*Shape*.—Individual flowers are urn shaped at the base, slightly flattened in one dimension, with stigmas flaring outward from the styles.

*Size*.—Individual flowers are 5 mm wide×8 mm tall.

*Flower buds*.—2 mm to 3 mm wide×3-5 mm long, ovoid.

*Color*.—Unopened buds: Greyed-purple 184A to Greyed-Purple 183B. Opened flower: The overall flower cluster appears Greyed-purple 183B, surrounded by bracts that are Red 46A to Red 53A.

*Petals and sepals*.—Reduced to a series of four each, very similar in appearance. Petals are oblong-obovate, 2 mm long×1 mm wide, have a smooth margin, and are Yellow-Green 153C on both surfaces. Petal tip is irregularly rounded. Sepals are oblong-obovate, 2 mm long×1 mm wide, have a smooth margin, with a color gradation on both surfaces from mostly Greyed-Yellow 160B in the center to Greyed-Red 179A on edges. Sepal tip broadly acute to irregularly rounded.

*Stamens*.—Nonfunctional. Reduced to a series of generally five, inside of petals and sepals. 1 mm high×0.5 mm wide. Stamens do not elongate beyond the corolla.

*Anthers*.—Non-functional, reduced to less than 1 mm, Greyed-Purple 185B.

*Pistil*.—A single pistil with two carpels. Style is short, 1 mm. The style divides near the base into two elongated, exerted stigmas, each 3 mm to 4 mm long×0.5 mm in diameter, velvety texture, Red 53A.

*Pollen*.—None.

*Pedicel*.—Length: 1 mm at the onset of flowering, extending up to 10 mm at the end of flowering. Diameter: 0.5 mm. Color: Yellow-green 145B when first emerging, then changing to Greyed-purple 185A as flowers and seeds mature. Surface texture: smooth.

*Pubescence*.—Flowers are glabrous except stigmas which are velvety and flower bud scales which are finely tomentose at the margins.

*Fragrance*.—None.

*Flowering date*.—Based on 2012 data for the original tree in Boring, Oreg. First bloom: March 22. Peak bloom: March 28. End of bloom: April 10.

*Fruit*.—Observations are from a sampling of typical fruit. The fruit is a samara, held in pairs by a pedicel in clusters of up to 5. However, because pollination is generally incomplete, it is more common that only a small percentage of the fruit actually develop, and therefore fruit clusters may contain as few as one or no samaras. Samaras that are not pollinated spontaneously abort and fall from the tree. The samara is attached at the seed end and the wings diverge at a 20 to 30 degree angle. The samaras are striated with a thickened, curved, keel on the outer edge with a thin and papery wing.

*Size*.—24-28 mm×9 mm×3 mm thick at seed end.

*Shape*.—Asymmetrically elongated with wing which becomes papery thin.

*Lenticels*.—None.

*Color*.—When first formed, samaras are Yellow-Green 150C to Yellow-Green 154D. As they ripen, they turn to Greyed-Orange 165B to Greyed-Orange 165C.

*Seeds*.—Oval, 6 mm×4 mm×2 mm thick, slightly pointed at the attachment end. Greyed-orange 165B to Greyed-Orange 166D.

*Fruit production*.—Sparse, few fruits produced, does not set fruit every year.

*Fruit maturity*.—Based on 2012 data, fruit matures and drops from tree May 20 to May 25.

*Usage*.—None.

Comparison to the species (unnamed, unpatented): My new variety has a strongly fastigiate branch habit that develops a canopy best described as tightly columnar to extremely narrow. Branches curve upward close to the main trunk becoming nearly vertical in orientation. Typical seedlings of the species have upright spreading branches and canopies that develop into a broadly oval to rounded shape. Data in the following three tables was all collected from trees growing in a nursery in Boring, Oreg. The upward curve of the branches of two year old trees of my new cultivar is illustrated by the data in TABLE 1, below. On two year old nursery row trees, branch crotch angles were measured as well as the degree of vertical orientation of branches, measured at 50 cm proximal to the branch tip. Measurements were made for mid canopy branches and the branches at the base of the canopy. The data illustrates that mid-canopy and basal branches of my cultivar begin with wide crotch angles and then quickly become much more vertical in orientation, whereas seedling trees maintain widely spreading angles of branch growth.

TABLE 1

| Feature: | 'JFS-KW78' | Seedling *A. rubrum* |
|---|---|---|
| Crotch angle, mid canopy branches | 70° to 90° | 45° to 80° |
| Crotch angle, canopy base | 90° | 60° to 90° |
| Branch angle degrees from vertical, 50 cm proximal to tip of mid-canopy branches | 10° to 30° | 40° to 80° |
| Branch angle degrees from vertical, 50 cm proximal to tip of lowest branches | 30° to 50° | 70° to 120° |
| Leaf blade size, average of 1 year tree in mid-canopy | 11.8 cm long × 11.1 cm wide | 15.8 cm long × 16.3 cm wide |
| Leaf tip | Long acuminate | Acute |
| Leaf tip narrowness, expressed as distance from tip to the point at which the central tip lobe is 1 cm wide, average | 4.1 cm | 1.6 cm |

Comparison to the seed parent: My new tree can be easily distinguished from its seed parent, *Acer rubrum* 'Armstrong', by its more compact, narrower form as illustrated by its slower growth rate, shorter branch length, and more vertical branch tip growth orientation. These and other differences are listed in Table 2.

TABLE 2

| Feature: | 'JFS-KW78' | 'Armstrong' |
|---|---|---|
| Bud break time, comparative | Late | Late |
| Mature tree shape | Tightly fastigiate, columnar to extremely narrow | Loosely fastigiate, narrow to narrowly oval |
| Growth rate | Moderate | Very fast |
| Height of 1 year trees, average | 188 cm | 232 cm |
| Height of 2 yr trees, average | 3.23 m | 4.30 m |
| Branch length, 1 year tree, average at 1 meter height | 18 cm | 95 cm |
| Branch length, 2 year tree, average of top four branches | 1.13 m | 2.07 m |

TABLE 2-continued

| Feature: | 'JFS-KW78' | 'Armstrong' |
|---|---|---|
| Branch angle degrees from vertical, 50 cm proximal to tip of mid-canopy branches of 2 year trees | 10° to 30° | 30° to 40° |
| Trunk diameter, 2 year tree, average at 10 cm height | 2.7 cm | 3.7 cm |
| Leaf blade size, average of 1 year tree in mid-canopy | 11.8 cm long × 11.1 cm wide | 17.2 cm long × 16.1 cm wide |
| Trunk color of 1 year tree at 1 meter, mid October | Greyed-Orange 163A to Greyed-Orange 164A | Yellow-Green 152A |

Comparison to most similar other cultivated varieties: My new tree can easily be distinguished from most other cultivars of *Acer rubrum* by its tightly fastigiate, narrow form. In addition to 'Armstrong', the seed parent of my new tree, there are four upright growing *Acer rubrum* cultivars that have some similarities to 'JFS-KW78'. In spring, the comparative time of bud break easily separates my tree from these four other cultivars, as my tree is later to break bud. Also, it has a tighter growth form than any cultivar except 'Columnare'. Table 3 shows a comparison of 'JFS-KW78' with these four cultivars, namely, 'Columnare', 'Scarsen', 'Karpick' and 'Bowhall', all of which are unpatented.

TABLE 3

| Feature: | 'JFS-KW78' | 'Columnare' | 'Scarsen' | 'Karpick' | 'Bowhall' |
|---|---|---|---|---|---|
| Bud break time, comparative | Late | Very early | Early | Middle | Very early |
| Mature tree shape | Tightly fastigiate, columnar to extremely narrow | Tightly fastigiate, columnar to very narrow | Upright narrow oval to oval | Upright ovate to broadly pyramidal | Tightly fastigiate, narrow |
| Leaf tip | Long acuminate | Acute to broadly acute | Acute to acuminate | Acuminate to long acuminate | Acute to acuminate |

I claim:

1. A new and distinct variety of red maple tree, substantially as herein illustrated and described.

* * * * *